United States Patent
Shah et al.

(10) Patent No.: US 9,005,508 B2
(45) Date of Patent: Apr. 14, 2015

(54) AIR DISENGAGEMENT ASSEMBLY AND METHOD FOR MANUFACTURING DIP-MOLDED ARTICLES OUT OF RTV SILICONE BY FULLY AUTOMATED PROCESS

(71) Applicant: Polyzen Inc., Apex, NC (US)

(72) Inventors: Tilak M. Shah, Cary, NC (US); Medhadakshina Murty Peri, Apex, NC (US)

(73) Assignee: Polyzen Inc., Apex, NC (US)

( * ) Notice: Subject to any disclaimer, the term of this patent is extended or adjusted under 35 U.S.C. 154(b) by 0 days.

(21) Appl. No.: 14/095,841

(22) Filed: Dec. 3, 2013

(65) Prior Publication Data

US 2014/0113060 A1 Apr. 24, 2014

Related U.S. Application Data

(62) Division of application No. 13/104,966, filed on May 10, 2011, now Pat. No. 8,597,012.

(60) Provisional application No. 61/333,287, filed on May 11, 2010.

(51) Int. Cl.
*B29C 41/14* (2006.01)
*B05C 11/00* (2006.01)
(Continued)

(52) U.S. Cl.
CPC . *B05C 11/00* (2013.01); *A61F 2/12* (2013.01); *A61F 2240/001* (2013.01); *A61M 25/1029* (2013.01); *B29C 41/14* (2013.01); *B29K 2019/00* (2013.01); *B05C 3/09* (2013.01)

(58) Field of Classification Search
USPC .................................................. 425/271, 272
See application file for complete search history.

(56) References Cited

U.S. PATENT DOCUMENTS 2,128,827 A 8/1938 Killian
3,013,302 A 12/1961 Croxton
(Continued)

FOREIGN PATENT DOCUMENTS

GB 315971 A 7/1929
GB 2217645 A 11/1989
(Continued)

OTHER PUBLICATIONS

Shah, T., "Dip Molding of Polyurethane and Silicone for Latex-Free, Nonallergenic Products", "http://www.mddionline.com/article/dip-molding-polyurethane-and-silicone-latex-free-nonallergenic-products", Apr. 2001, Publisher: Medical Device and Diagnostic Industry (MDDI).

*Primary Examiner* — Benjamin Schiffman
(74) *Attorney, Agent, or Firm* — Hultquist, PLLC; Steven J. Hultquist

(57) ABSTRACT

An automated mandrel dip coating process assembly for RTV silicone dispersions is described, including an enclosure adapted to hold a moisture-cure ambient temperature curable medium for mandrel dip molding and at least one mandrel having a surface for contacting the moisture-cure ambient temperature curable medium. An automated motive drive assembly is arranged to removably translate one or more of the mandrel(s) into contact with the moisture-cure ambient temperature curable medium in the enclosure, and to subsequently translate at least one mandrel contacted with the moisture-cure ambient temperature curable medium into at least one of (A) contact with a bubble crusher in the enclosure, and (B) disengagement from the moisture-cure ambient temperature curable medium in the enclosure and rotation of the mandrel at a vertical displacement angle of from 70° to 110°. By such arrangement, air bubble entrapment on the dip molded film on the mandrel is avoided, and controlled film thickness is achieved at desired location(s) so that the product molded film article is free of pinholes and air bubble inclusions in the film, and complies with desired thickness specifications.

13 Claims, 5 Drawing Sheets

(51) Int. Cl.
*B05C 3/09* (2006.01)
*A61F 2/12* (2006.01)
*A61M 25/10* (2013.01)
*B29K 19/00* (2006.01)

(56) References Cited

U.S. PATENT DOCUMENTS

| | | |
|---|---|---|
| 3,661,156 A | 5/1972 | McLaughlin |
| 3,708,324 A | 1/1973 | Stebleton |
| 3,769,983 A | 11/1973 | Merav |
| 3,978,187 A | 8/1976 | Fletcher et al. |
| 4,043,345 A | 8/1977 | Kramann et al. |
| 4,650,463 A | 3/1987 | LeVeen et al. |
| 4,784,133 A | 11/1988 | Mackin |
| 4,946,464 A | 8/1990 | Pevsner |
| 5,091,442 A | 2/1992 | Milner |
| 5,116,310 A | 5/1992 | Seder et al. |
| 5,219,792 A | 6/1993 | Kim et al. |
| 5,360,414 A | 11/1994 | Yarger |
| 5,433,252 A | 7/1995 | Wolf et al. |
| 5,545,220 A | 8/1996 | Andrews et al. |
| 5,554,673 A | 9/1996 | Shah |
| 5,562,720 A | 10/1996 | Stern et al. |
| 5,679,423 A | 10/1997 | Shah |
| 5,715,839 A | 2/1998 | Strauss et al. |
| 5,718,236 A | 2/1998 | Curcio |
| 5,826,588 A | 10/1998 | Forman |
| 5,833,915 A | 11/1998 | Shah |
| 5,879,499 A | 3/1999 | Corvi |
| 5,924,456 A | 7/1999 | Simon |
| 5,996,639 A | 12/1999 | Gans et al. |
| 6,022,313 A | 2/2000 | Ginn et al. |
| 6,249,708 B1 | 6/2001 | Nelson et al. |
| 6,291,543 B1 | 9/2001 | Shah |
| 6,312,405 B1 | 11/2001 | Meyer et al. |
| 6,329,444 B1 | 12/2001 | McGlothlin et al. |
| 6,352,077 B1 | 3/2002 | Shah |
| 6,443,947 B1 | 9/2002 | Marko et al. |
| 6,478,789 B1 | 11/2002 | Spehalski et al. |
| 6,488,654 B2 | 12/2002 | Gonzalez et al. |
| 6,607,545 B2 | 8/2003 | Kammerer et al. |
| 6,805,662 B2 | 10/2004 | Shah et al. |
| 6,827,710 B1 | 12/2004 | Mooney et al. |
| 6,875,193 B1 | 4/2005 | Bonnette et al. |
| 7,220,252 B2 | 5/2007 | Shah |
| 7,470,251 B2 | 12/2008 | Shah |
| 8,597,012 B2 | 12/2013 | Shah et al. |
| 2002/0072707 A1 | 6/2002 | Gonzalez et al. |
| 2002/0082634 A1 | 6/2002 | Kammerer et al. |
| 2003/0088209 A1 | 5/2003 | Chiu et al. |
| 2005/0222329 A1 | 10/2005 | Shah |
| 2006/0212064 A1 | 9/2006 | Shah |
| 2007/0212559 A1 | 9/2007 | Shah |
| 2007/0239110 A1 | 10/2007 | Shah |
| 2007/0299463 A1 | 12/2007 | Shah |
| 2008/0114210 A1 | 5/2008 | Shah et al. |
| 2008/0188802 A1 | 8/2008 | Shah |
| 2008/0262449 A1 | 10/2008 | Shah et al. |
| 2008/0262450 A1 | 10/2008 | Shah et al. |
| 2009/0082724 A1 | 3/2009 | Shah et al. |

FOREIGN PATENT DOCUMENTS

| | | |
|---|---|---|
| JP | 51-90376 A | 8/1976 |
| JP | 51-100833 A | 9/1976 |
| JP | 51-101084 A | 9/1976 |
| JP | 10-127771 A | 5/1998 |

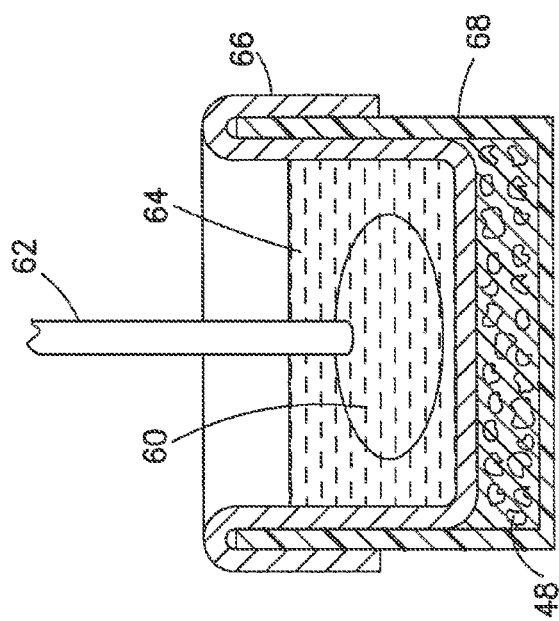
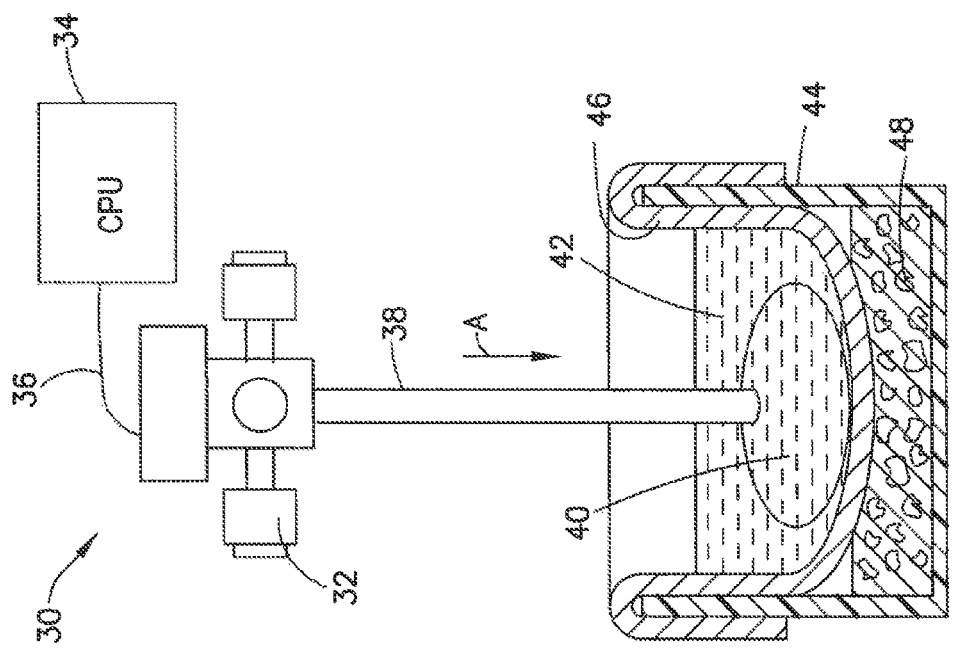
FIG.3
FIG.4

AIR DISENGAGEMENT ASSEMBLY AND METHOD FOR MANUFACTURING DIP-MOLDED ARTICLES OUT OF RTV SILICONE BY FULLY AUTOMATED PROCESS

CROSS-REFERENCE TO RELATED APPLICATIONS

This application is a divisional under 35 USC 120 of U.S. patent application Ser. No. 13/104,966 filed May 10, 2011, and issued Dec. 3, 2013 as U.S. Pat. No. 8,597,012, which in turn claims the benefit of priority under 35 USC 119 of U.S. Provisional Patent Application No. 61/333,287 filed on May 11, 2010. The disclosures of such U.S. patent application Ser. No. 13/104,966 and U.S. Provisional Patent Application No. 61/333,287 are hereby incorporated herein by reference in their respective entireties, for all purposes.

FIELD OF THE INVENTION

The present invention relates to an air disengagement assembly for removing entrapped air bubbles from dip molded polymeric films formed on mandrel surfaces, and to a corresponding method of manufacturing dip-molded articles out of RTV silicones and other such moisture sensitive and curable polymeric resins that are free of air bubble inclusions, pin-holing and other film defects resulting from entrapment of air during a fully automated dip molding process.

DESCRIPTION OF THE RELATED ART

In the practice of manufacturing dip molded thin film polymeric articles, when utilizing ambient cure polymeric resins such as Room temperature vulcanizable moisture-cure (RTV) silicones, there is a tendency for the dip molded film formed on the mandrel to entrap air in the film. This tendency typically manifests itself on a bottom surface or lower extremity of the mandrel, resulting from air being "caught" on the surface of the mandrel as the mandrel is lowered into a bath or reservoir of resin material.

In manual dip molding operations, this tendency for entrapment of air is addressed by inserting a mandrel in the resin bath at an oblique angle so that air can readily disengage from the surface of the mandrel. The manual operator thereafter may perform a swirling or other arcuate movement with the mandrel in the resin and subsequently while the mandrel is being manually moved to an ultimate inverted position with the mandrel shaft then being positioned in a receiving opening in a drying stand or fixture.

Although such manual movements may be effective in disengaging air bubbles from the surface of the mandrel during and subsequent to the dipping operation, manual dip molding is inherently a slow, inefficient, operator-dependent, variable thickness (e.g., thin dome and thick portions) and uneconomic process.

It would therefore be desirable to automate the dip molding process in a manner in which disengagement of air from mandrel surfaces is achieved in a highly efficient and reproducible fashion, with a desired uniform thickness distribution being achieved within a specification of narrow range, and in a economic manner, using materials such as RTV silicones which typically have very short shelf life and start curing as soon as they are exposed to humidity.

SUMMARY OF THE INVENTION

The present invention relates to dip molding systems and methods, in which air entrapment in the dip molded film is avoided.

In one aspect, the invention relates to an automated mandrel coating assembly, comprising:
(a) an enclosure adapted to hold an ambient temperature curable medium, e.g., a moisture-cure ambient temperature curable medium, for mandrel dip molding;
(b) at least one mandrel having a surface for contacting the ambient temperature curable medium; and
(c) an automated motive drive assembly arranged to:
(i) removably translate one or more of said at least one mandrel into contact with the ambient temperature curable medium in the enclosure, and
(ii) subsequently translate the at least one mandrel contacted with the ambient temperature curable medium into at least one of (A) contact with a bubble crusher in the enclosure, and (B) disengagement from the ambient temperature curable medium in the enclosure and rotation of the at least one mandrel at a vertical displacement angle of from 70° to 110°.

The translation (i) and (ii) can be carried out one or more times to achieve a desired thickness of the ambient temperature curable medium.

In another aspect, the invention relates to a mandrel coating method, comprising:
providing an enclosure adapted to hold an ambient temperature curable medium, e.g., a moisture cure ambient temperature curable medium, for mandrel dip molding;
actuating an automated motive drive assembly to translate at least one mandrel into contact with an ambient temperature curable medium in said enclosure for coating of said mandrel with such curable medium; and
thereafter, by continued action of said motive drive assembly, translating the at least one mandrel contacted with the ambient temperature curable medium into at least one of (A) contact with a bubble crusher in the enclosure, and (B) disengagement from the ambient temperature curable medium in the enclosure and rotation of the at least one mandrel at a vertical displacement angle of from 70° to 110°. As noted above, the mandrel translation can be carried out one or more times to achieve a desired thickness of the ambient temperature curable medium.

The disclosure in other aspects relates to an automated mandrel coating assembly, and mandrel coating method in which the ambient temperature curable medium is a moisture-curable ambient temperature curable medium.

Still other aspects, features and embodiments of the invention will be more fully apparent from the ensuing disclosure and appended claims.

BRIEF DESCRIPTION OF THE DRAWINGS

FIG. 3 is a simplified schematic elevation view of a part of the dip molding apparatus according to one embodiment of the invention, for eliminating air bubble entrapment on lower surfaces of the mandrel being contacted with the dip molding polymeric material.

FIG. 4 is a schematic elevation view of a dip molding mandrel disposed in a resin volume in an enclosure, to coat surfaces of the mandrel with the resin material.

DETAILED DESCRIPTION OF THE INVENTION, AND PREFERRED EMBODIMENTS THEREOF

Figure 1:
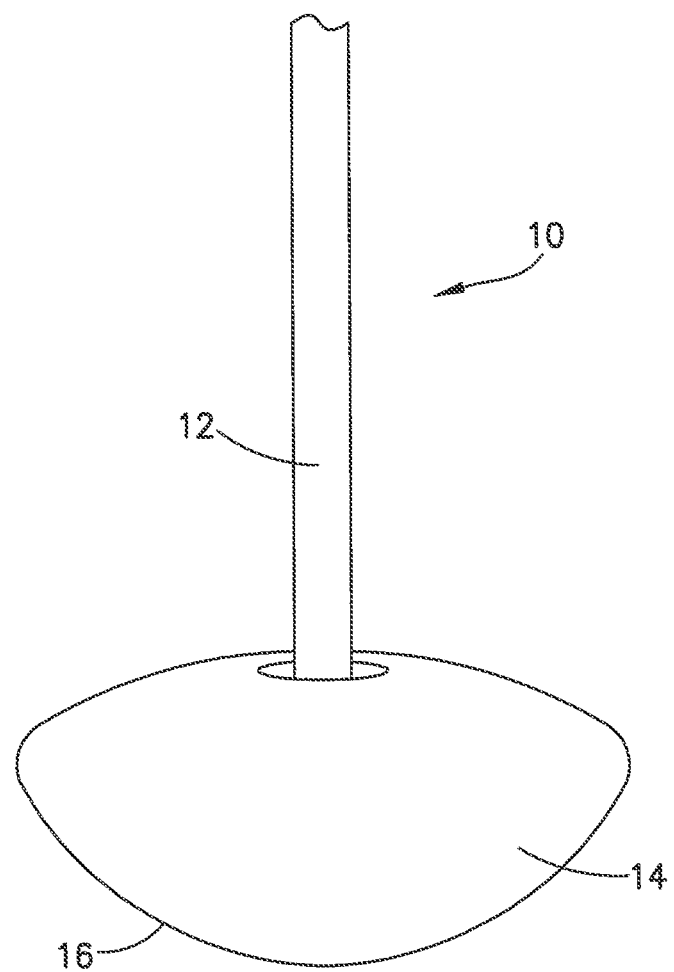
FIG. 1 is an elevation view of a dip molding mandrel useful for forming polymeric breast prostheses from ambient temperature curing moisture-cure silicone resins.

The present invention relates to a fully automated dip molding process and apparatus, and to dip molding system arrangements for RTV silicone to make shells for breast implant and/or other similar shape devices in which air bubble entrapment in dip molded films is eliminated in a highly efficient and cost-effective manner.

In one aspect, the invention relates to a mandrel coating assembly, comprising:
(a) an enclosure adapted to hold a moisture-cure ambient temperature curable medium for mandrel dip molding;
(b) at least one mandrel having a surface for contacting the moisture-cure ambient temperature curable medium; and
(c) an automated motive drive assembly arranged to:
  (i) removably translate one or more of said at least one mandrel into contact with the moisture-cure ambient temperature curable medium in the enclosure, and
  (ii) subsequently translate the at least one mandrel contacted with the moisture-cure ambient temperature curable medium into at least one of (A) contact with a bubble crusher in the enclosure, and (B) disengagement from the moisture-cure ambient temperature curable medium in the enclosure and rotation of the at least one mandrel at a vertical displacement angle of from 70° to 110°.

The translation (i) and (ii) can be carried out one or more times to achieve a desired thickness of the moisture-cure ambient temperature curable medium.

Thus, in such mandrel coating assembly, the motive drive assembly can be arranged to translate the at least one mandrel contacted with the moisture-cure ambient temperature curable medium into contact with a bubble crusher in the enclosure.

Alternatively, the motive drive assembly can be arranged to translate the mandrel(s) contacted with the moisture-cure ambient temperature curable medium into disengagement from the moisture-cure ambient temperature curable medium in the enclosure and rotation of the at least one mandrel at a vertical displacement angle of from 70° to 110°. As used herein, the term "vertical displacement angle" refers to the angle subtended by a vertical axis and the centerline of a shaft of a mandrel in an ambient exposure and drying condition of the polymeric film formed on the mandrel by the dipping operation.

In one specific arrangement, the mandrel coating assembly utilizes a motive drive assembly that is arranged to translate the at least one mandrel contacted with the moisture-cure ambient temperature curable medium into contact with a bubble crusher in the enclosure, and to also translate the at least one mandrel contacted with the moisture-cure ambient temperature curable medium into disengagement from the moisture-cure ambient temperature curable medium in the enclosure and rotation of the at least one mandrel at a vertical displacement angle of from 70° to 110°.

The mandrel may be of any suitable type and construction, appropriate to the end-use application thereof. The mandrel may for example constitute a form or body mounted on a shaft, so that the shaft can be coupled with a motive driver assembly arranged to contact the mandrel with the polymeric resin, following which the mandrel is retracted from the resin bath, and may remain vertically or angularly oriented, or alternatively may be swung to a laterally extending position.

By way of example, in one embodiment, the mandrel may comprise a form that is manufactured from a polyacetal resin, having a smooth low surface energy surface facilitating film formation thereon and tearing of the applied resin material when the dip coating film on the mandrel is exposed to the ambient environment of the dipping apparatus.

The mandrel may comprise a single mandrel, or alternatively a multiplicity of mandrels in an array. The motive driver assembly is suitably coupled with individual ones, or more than one, of mandrels, to effectuate movement, as hereinafter described in fuller detail. Thus, the motive driver assembly may be arranged to synchronously translate each multiple mandrels in a same translational path.

The resin bath may be provided in an enclosure of a size and shape to accommodate a multiplicity of mandrels, e.g., in the aforementioned array form, within the interior volume of the bath. Alternatively, a multiplicity of mandrels may be provided, with each one of the multiplicity of mandrels having a separate individual enclosure adapted to hold a moisture-cure ambient temperature curable medium for mandrel dip molding. In other words, each of the mandrels thereby has its own reservoir with which it is engaged for the dip coating operation.

The moisture-cure ambient temperature curable medium may thus be provided in suitable volume in the enclosure arranged to receive one or more mandrels for dip coating operation. The moisture-cure ambient temperature curable medium may be of any suitable type, e.g., an ambient temperature curable silicone material, of a type frequently referred to as a room temperature vulcanizable silicone or RTV silicone.

In the implementation of the invention in which a bubble crusher is employed, the crushing of the bubble or bubbles may be carried out with simple contact with a suitable material effective to disengage the bubble(s) from the polymeric film. Such simple contact may be effected without substantial application of force, but with sufficient contact so that the bubble(s) on the film surface on the mandrel are compacted to release the air bubble(s). The contact can be carried out at any suitable conditions. In one embodiment, the contacting is carried out at or below ambient temperature and pressure conditions. The formulation of the film-forming material to be applied to the dip molding mandrel can be of any suitable type. The formulation may for example constitute a simple solvent formulation of silicone or silicone precursor material, with xylene commonly being employed in formulations of RTV silicone materials. The formulation may for example be devoid of any fibers or reinforcement media.

The bubble crusher in one implementation includes a resiliently deformable material that is arranged for contact with the mandrel surface to crush air bubbles entrapped in said moisture-cure ambient temperature curable medium thereon. The resiliently deformable material may be of any suitable type, and can for example include sponge material, or alternatively an elastomeric material of synthetic or natural character, or a gel pad, a packet containing particulate material, a deformable bladder filled with liquid or gas medium, or any other suitable material(s) and construction(s) providing resilient deformability when contacted with the mandrel. By the resilient deformable character of the contact material, damage to the mandrel is avoided.

The flexible resilient material such as sponge material may be arranged as a layer on a floor of the enclosure containing the resin material in which the mandrel is to be dip coated.

In a further aspect, the invention contemplates use of an enclosure for the resin bath, in which a liner is utilized to hold the dip coating material in the enclosure. For this purpose, a solvent-resistant liner material may be simply draped over the circumscribing walls of the enclosure, so that the interior surfaces of the enclosure are covered by the liner and the liner is folded back over the upper ends of the walls of the enclosure to form a receptacle structure for the dip coating resin.

The use of a liner in such manner facilitates cleanup and shutdown of the dip molding system, particularly since the ambient temperature curable moisturizing cure silicone formulations used in dip molding applications are formulations having a typical pot life on the order of 6-12 hours, or under some special conditions up to 48 hours, so that after such duration has passed, the formulation will be partially thickened or set up in the liner, and become solid or semisolid in character and unusable. At this point, the edges of the liner can be readily grasped and the liner and set up dip molding material may be unitarily disposed of, without the disadvantages of cleaning the enclosure utilized in the dip molding operation.

The motive drive assembly utilized in the practice of the invention to motivate translate the mandrel or mandrels, can be constructed and arranged to effect vertical reciprocating movement, for inserting the mandrel into the dip coating enclosure for contact with dip coating material therein, and subsequent retraction of the mandrel from the enclosure to expose the dip coating material on the mandrel to the ambient environment for curing thereof. The motive drive assembly may further be constructed and arranged to provide the ability to rotate the shaft, as well as the ability to swing the shaft toward or to any suitable orientation. For this purpose, the motive drive assembly may be coupled with the mandrel with suitable gearing, gimbles, fittings, joints, etc. so as to permit the mandrel to be translated in any of various directions, including to a horizontal or generally horizontal orientation of the mandrel shaft, relative to the vertical. The dip coating system can also include a pallet that is omnirotational through an angular range of 0-360°.

The motive drive assembly may be arranged with a central processing unit or other controller or processor, so that the motive drive assembly translates the mandrel or mandrels according to a programmatic sequence or protocol. For example, the motive drive assembly may be programmably arranged to translate the mandrel(s) for curing of a moisture-cure ambient temperature curable medium on the mandrel and exposure to an ambient air environment of the mandrel coating assembly. In a specific implementation, the motive drive assembly may be programmably arranged for translation of the mandrel for exposure to the ambient air environment of the mandrel coating assembly according to a temperature/humidity/time relationship, so that the time, temperature and humidity operate as processing variables to govern the speed of processing in the dip molding operation.

The motive drive assembly can be arranged to rotate the mandrel about the axis of its shaft, and to adjust the attitude of the shaft in relation to the vertical so that for example the shaft may be at a vertical displacement angle in a range of from 70° to 110° as has been found to be highly effective in disengaging air bubbles and facilitating the production of pinhole- and bubble-free, controlled thickness, thin film silicone articles such as shells for breast prosthetic devices, other medical balloon devices, and the like.

The dip coating operation may be carried out to provide dip coated film articles of any suitable type, structure, conformation and thickness. For example, the motive drive assembly can be programmatically arranged to provide transitional movement of the mandrel subsequent to disengagement from the dip coating bath, which minimizes the thickness gradients in the product article, or alternatively, provides a specific desired gradient across extremities or regions of the product article. By way of specific example, silicone breast prostheses may be manufactured utilizing the system and method of the invention, with film thickness in a range of from 14 to 30 mils, more preferably in a range of from 14 to 20 mils, and most preferably in a range of from 15 to 18 mils.

Although the foregoing description has been mainly directed to utilization of room temperature curable moisturizing cure silicone dip coating formulations, it will be recognized that the utility of the invention is not thus limited, but rather extends to and includes utilization of any other dip coating materials, including HTV silicones, polyurethanes, other organic solvent based polymer dispersions, etc. Preferred materials include RTV silicone dispersions such as MED 6605, commercially available from Nusil Corporation, or silicone dispersion 40001, commercially available from Applied Silicone, Inc. High temperature vulcanizable (HTV) silicone materials can also be employed in the practice of the invention.

In various specific embodiments, the apparatus and method of the present disclosure can be utilized to form a wide variety of products from dip coating materials of correspondingly diverse character. Various medical devices are usefully formed, including implantable medical devices. Illustrative implantable medical devices include breast implants, e.g., saline solution-filled breast implants, space-occupying balloon device implants, and non-silicone gel filled implants. Such medical device implants can be formed of any suitable dip-molding composition. The dip-molding process of the present disclosure can reliably and reproducibly form thin-wall product articles, such as product articles having a wall thickness that is less than 0.30 inch (0.76 cm), e.g., thickness in a range of from 0.05 inch (0.13 cm) to 0.28 inch (0.71 cm).

Although the disclosure herein is directed primarily to the use of a moisture-cure ambient temperature curable medium for mandrel dip molding, it will be appreciated that the ambient temperature curable medium may be of a moisture-cure type or alternatively it may be a curable medium of other suitable type.

In one method aspect, the invention can be carried out to perform a mandrel coating including:
providing an enclosure adapted to hold a moisture-cure ambient temperature curable medium for mandrel dip molding;
actuating a motive drive assembly to translate at least one mandrel into contact with a moisture-cure ambient temperature curable medium in said enclosure for coating of the mandrel with such curable medium; and
thereafter, by continued action of the motive drive assembly, translating the at least one mandrel contacted with the moisture-cure ambient temperature curable medium into at least one of (A) contact with a bubble crusher in the enclosure, and (B) disengagement from the moisture-cure ambient temperature curable medium in the enclosure and rotation of the at least one mandrel at a vertical displacement angle of from 70° to 110°, wherein the mandrel translation is carried out one or more times to achieve a desired thickness of the moisture-cure ambient temperature curable medium.

The method may be carried out such that at least one mandrel is contacted with a bubble crusher in the enclosure, e.g., wherein the bubble crusher includes a resiliently deformable material arranged for contact with the mandrel surface to crush air bubbles entrapped in the moisture cure ambient temperature curable medium thereon.

As discussed, the resiliently deformable material may comprise a sponge material, e.g., arranged as a layer on a floor of the enclosure in the dip coating system, optionally including liner in the enclosure to hold the moisturizing cure ambient temperature curable material therein. In such methodology, the motive drive assembly may be suitably programmably arranged to translate at least one mandrel for curing of the moisture-cure ambient temperature curable medium on the mandrel in exposure to an ambient air environment of the mandrel coating assembly. As mentioned, the motive drive assembly can be programmably arranged for translation of the mandrel(s) for exposure to said ambient air environment of the mandrel coating assembly according to a temperature/humidity/time relationship.

Referring now to the drawings, FIG. 1 is an elevation view of a dip molding mandrel 10 useful for forming polymeric breast prostheses from ambient temperature curing moisture-cure silicone resins. The mandrel 10 includes a mandrel body 14 having a surface 16 to be coated with the dip coating material to form a cured thin film material thereon. The mandrel body 14 is coupled to the lower end of a shaft 12 to permit the mandrel body to be rotated at a desired rotational speed during the dipping and/or subsequent curing (ambient exposure).

Figure 2:
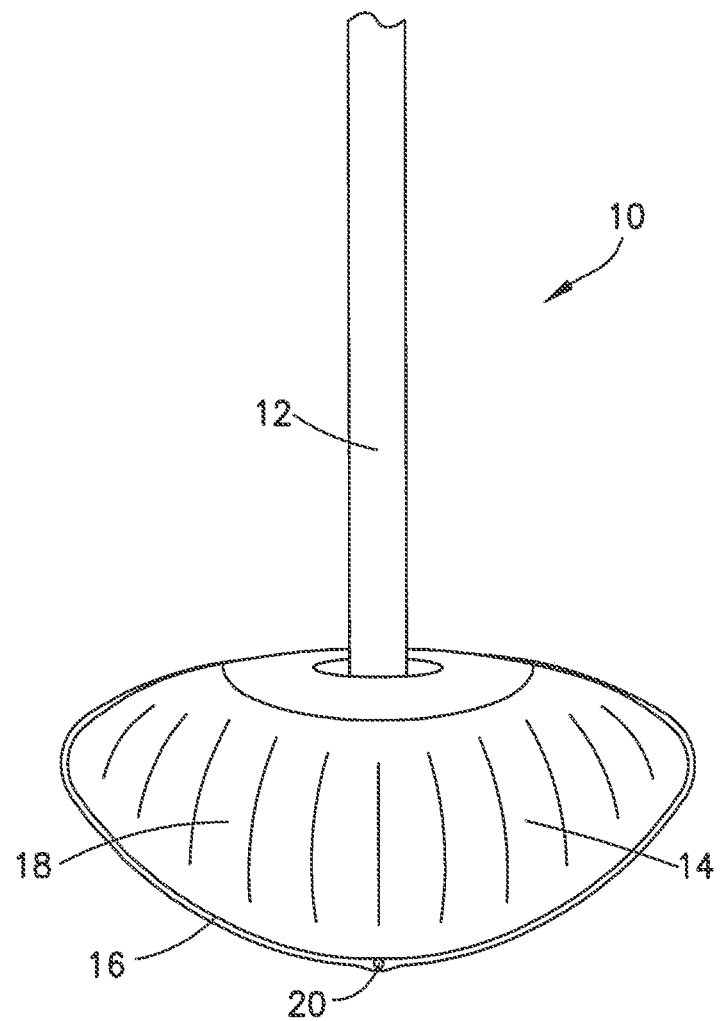
FIG. 2 is an elevation view of the dip molding mandrel of a type as shown in FIG. 1, on which a dip molded film has been formed, having an entrapped air bubble at a lower surface of the mandrel.

FIG. 2 is an elevation view of the dip molding mandrel 10 of a type as shown in FIG. 1, on which a dip molded film 18 has been formed, having an entrapped air bubble 20 at a lower surface of the mandrel. All parts in FIG. 2 are numbered correspondingly to FIG. 1

FIG. 3 is a simplified schematic elevation view of a dip molding apparatus 30 according to one embodiment of the invention, for eliminating air bubble entrapment on lower surfaces of the mandrel 40 being contacted with the dip molding polymeric material 42. The apparatus 30 includes an enclosure 44 having an open top, on the floor of which is a sponge 48. The sponge 48 covers the floors and lower portions of the side walls of the enclosure container, and a liner 46 is disposed in the interior of the enclosure 44 so that the liner holds the dip molding material 42.

The sponge 48 thus forms a layer in the lower portion of the container 44. The mandrel 40 is joined to the lower end of a shaft 38 as illustrated. The shaft in turn is coupled to the motive drive assembly 32 which is shown in simplified schematic form for ease of discussion, and the motive drive assembly 32 in turn is joined to central processing unit (CPU) 34 via signal transmission line 36, whereby the motive driver assembly may be actuated by appropriate signal from the CPU to carry out a predetermined process sequence. The sequence may involve, in the illustrative embodiment, a downward translation of the shaft 38 under the control of the motive driver assembly 32, so that the shaft is translated downwardly in the direction indicated by arrow A. In such down position, the mandrel 40 reposes on the liner 46 and acts to press on the liner and underlying sponge, so that the sponge compresses. Any air bubbles on the bottom surface of the mandrel thereby are broken by the contact of the mandrel surface with the deformable and compressible sponge. The mandrel thereby is protected from damage that would otherwise occur if the liner and resilient sponge were not present.

Once the mandrel has contacted the liner and sponge, e.g., up to a certain depth or under a certain pressure, the mandrel is retracted from the enclosure 44, in the direction opposite that indicated by arrow A in FIG. 1. The mandrel may be thereafter translated to any suitable position, with or without rotation of the mandrel by the motive drive assembly.

One significant benefit of utilizing an enclosure 44 that is sized closely to the mandrel 40 is that reduced amounts of resin and be utilized. Further, the mandrel in FIG. 3 when fully submerged in the resin will cause the level of resin to rise, so that coating of the entire top and bottom surfaces with the resin is achieved with a relatively small amount of resin.

FIG. 4 is a schematic elevation view of a dip molding mandrel 60 disposed in a resin volume 64 in an enclosure, to coat surfaces of the mandrel 60 with the resin material. The mandrel is joined to the lower end of a shaft 62 in an enclosure 68. The enclosure contains a liner 66, which in turn holds the resin material 64.

Figure 5:
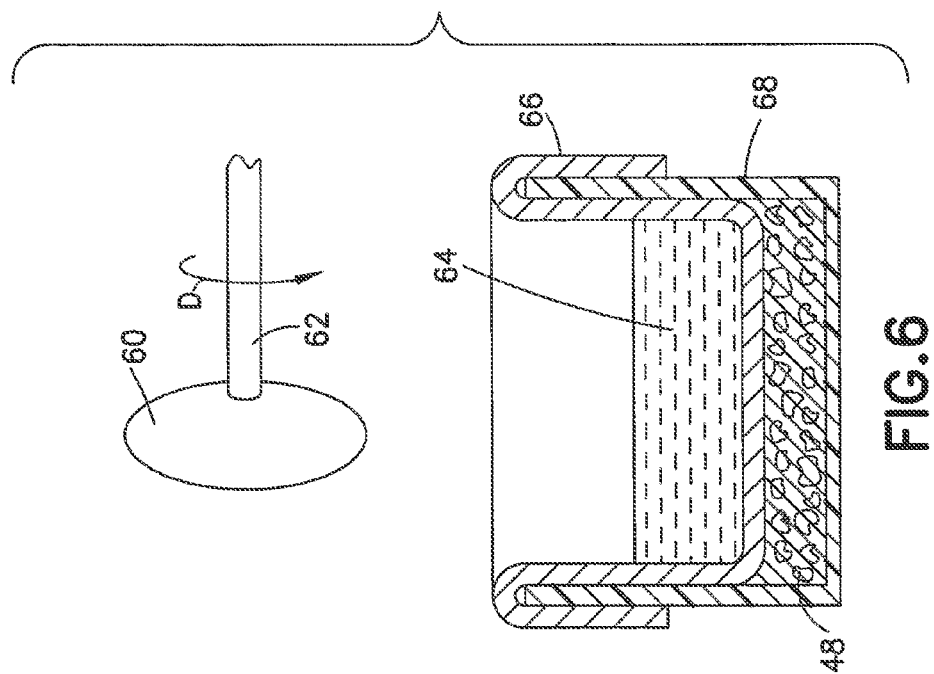
FIG. 5 is a schematic elevation view of a part of the dip molding apparatus of FIG. 4, wherein the mandrel has been vertically retracted from the resin bath.

FIG. 5 is a schematic elevation view of the dip molding apparatus of FIG. 4, wherein the mandrel 60 has been vertically retracted from the resin bath on shaft 62, in the direction indicated by arrow B in FIG. 5. During this time, the mandrel may be rotated, e.g., in the direction indicated by arrow C, to assist in curing the resin by ambient air exposure thereof.

The shaft 62 is shown as being rotated in the direction of the arrowhead by arrow C, but the shaft in an alternative mode of operation may be free of rotation movement throughout the entire sequence of process steps.

Figure 6:
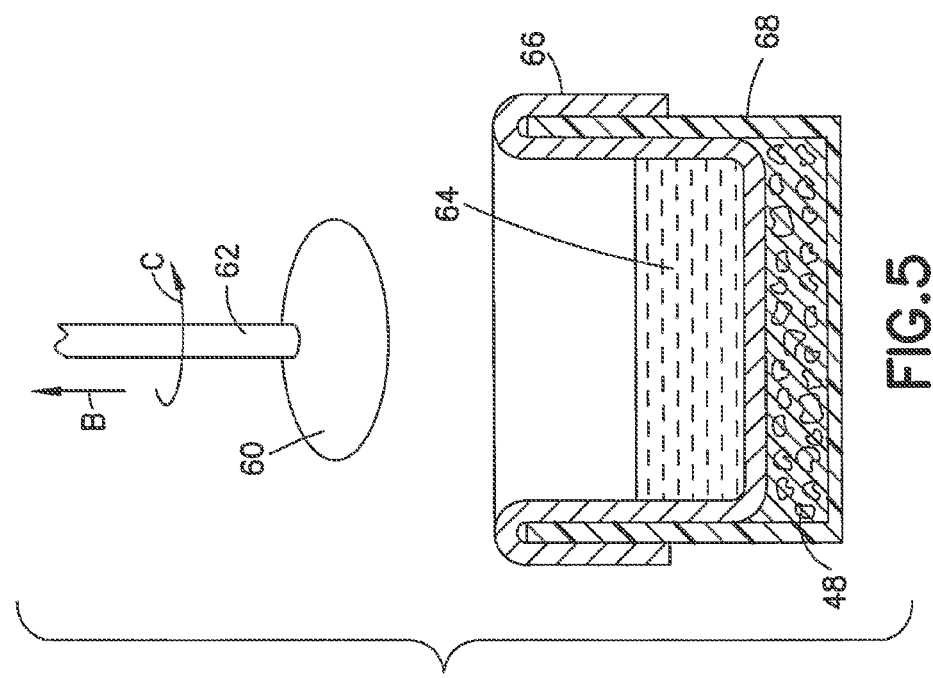
FIG. 6 is a schematic elevation view of a part of the dip molding apparatus of FIGS. 4-5, wherein the mandrel has been rotated from the vertical position shown in FIG. 5 to a generally horizontal position, while the mandrel shaft is being rotated.

FIG. 6 is a schematic elevation view of the dip molding apparatus of FIGS. 4-5, wherein the mandrel has been rotated from the vertical position shown in FIG. 5 to a generally horizontal position, while the mandrel shaft is being rotated. All reference numerals in FIG. 6 are numbered correspondingly to FIGS. 4-5.

Figure 7:
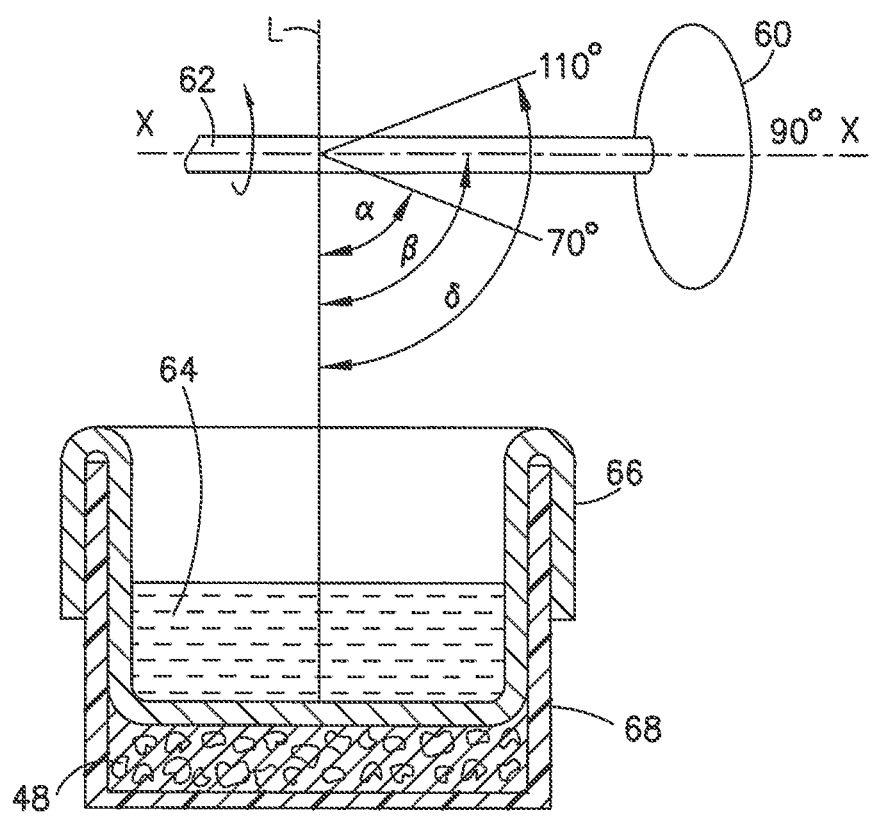
FIG. 7 is a schematic elevation view of a part of the dip molding apparatus of FIGS. 4-6, showing the vertical displacement angles α, β, and δ at which rotation of the mandrel can take place.

FIG. 7 is a schematic elevation view of a portion of the dip molding apparatus of FIGS. 4-6, showing the vertical displacement angles $\alpha$, $\beta$, and $\delta$ at which rotation of the mandrel can take place. All reference numerals in FIG. 7 are numbered correspondingly to FIGS. 4-6. As illustrated, the vertical displacement angles are measured with respect to the vertical, depicted as line L, from which angles $\alpha$, $\beta$ and $\delta$ are measured. Angle $\alpha$ is shown as 70°, angle $\beta$ is shown as 90° and angle $\delta$ is shown as 110°. When using RTV silicone resins, use of a vertical displacement angle of from 70° to 110° is highly favorable for achieving controlled thickness of film at desired location(s) of the product article, as well as for effecting disengagement of air bubbles from the dip coated material on the mandrel, and producing a cured film article of superior character. In the drawing of FIG. 7, the central axis of the shaft 62 is shown as centerline L-L.

The above dip coating cycle can be repeated as needed to build a desired thickness of polymeric film, layer by layer, to meet product device specifications. For example, the apparatus and method of the invention can be conducted in a fully automated process for manufacturing thin film RTV silicone shells for saline-filled breast implant articles having thickness in a range of from 10 to 30 mils, by multiple dip cycles.

The invention can be practiced with a dip molding apparatus that is configured with an enclosure and door assembly that is coordinated with movement of the mandrel(s) so that exposure of the film-forming composition to the ambient environment (atmospheric humidity) is minimized. The dip molding apparatus may be arranged so that as the mandrel retracts from the reservoir containing the film-forming material, excess liquid is drained, so that partially cured liquid will not contaminate the liquid material in the reservoir. The door may be arranged to selectively close so that when the coated mandrel is exposed to higher heat and humidity required for the specific time-temperature-humidity profile, the humidity-sensitive liquid in the reservoir is protected from the severe environment to which the coated material on the mandrel is exposed. Before and after the door closes, an inert gas purge blankets the moisture-sensitive coating material in the reservoir, such that the material in the reservoir is protected from the ambient air on the surface of the reservoir liquid during door opening and dipping operations.

The apparatus can include a mandrel with x, y, z rotational capabilities, and can be programmed to operate at any angle from 0 to 360°. When the mandrel is retracted from the coating liquid, the mandrel may be maintained at an angle of 180° for an extended period of time. The mandrel may be rotated about its central axis during mandrel translation, to the extent necessary or desirable to achieve the specific dip coating manufacture of a specific dip-coated product article.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A mandrel coating method, comprising:
    providing an enclosure adapted to hold a moisture-cure ambient temperature curable medium for mandrel dip molding;
    actuating a motive drive assembly to translate at least one mandrel into contact with a moisture-cure ambient temperature curable medium in said enclosure for coating of said mandrel with such curable medium; and
    thereafter, by continued action of said motive drive assembly, translating the at least one mandrel contacted with the moisture-cure ambient temperature curable medium into at least one of (A) contact with a bubble crusher in the enclosure, and (B) disengagement from the moisture-cure ambient temperature curable medium in the enclosure and rotation of the at least one mandrel at a vertical displacement angle of from 70° to 110°.

2. The method of claim 1, wherein the at least one mandrel is contacted with a bubble crusher in the enclosure.

3. The method of claim 2, wherein the bubble crusher includes a resiliently deformable material arranged for contact with the mandrel surface to crush air bubbles entrapped in said moisture-cure ambient temperature curable medium thereon.

4. The method of claim 3, wherein said resiliently deformable material comprises sponge material.

5. The method of claim 4, wherein said sponge material is arranged as a layer on a floor of the enclosure.

6. The method of claim 1, including a solvent-resistant liner in said enclosure to hold the moisture-cure ambient temperature curable medium therein.

7. The method of claim 1, wherein said motive drive assembly is programmably arranged to translate said at least one mandrel for curing of said moisture-cure ambient temperature curable medium on the mandrel in exposure to an ambient air environment of the mandrel coating assembly.

8. The method of claim 7, wherein said motive drive assembly is programmably arranged for translation of said mandrel for said exposure to said ambient air environment of the mandrel coating assembly according to a temperature/humidity/time relationship.

9. The method of claim 1, wherein said motive drive assembly is arranged to rotate one or more of said at least one mandrel.

10. The method of claim 1, wherein said motive drive assembly is arranged to rotate said at least one mandrel during curing of the moisture-cure ambient temperature curable medium thereon.

11. The method of claim 1, as carried out to manufacture an implantable medical device.

12. The method of claim 11, wherein the implantable medical device comprises a device selected from the group consisting of breast implants, saline solution-filled breast implants, space-occupying balloon devices, and non-silicone gel filled devices.

13. The method of claim 11, wherein the implantable medical device comprises a thin-wall device having wall thickness of less than 0.30 inch (0.76 cm).

* * * * *